United States Patent
Bhushan et al.

(10) Patent No.: US 9,616,127 B2
(45) Date of Patent: Apr. 11, 2017

(54) METHOD AND TOPICAL FORMULATION FOR TREATING LOCALIZED EDEMA

(75) Inventors: Rajiv Bhushan, Palo Alto, CA (US); Jerry B. Gin, Sunnyvale, CA (US); Amit Goswamy, Los Gatos, CA (US)

(73) Assignee: Livionex Inc., Los Gatos, CA (US)

( * ) Notice: Subject to any disclaimer, the term of this patent is extended or adjusted under 35 U.S.C. 154(b) by 1335 days.

(21) Appl. No.: 12/581,678

(22) Filed: Oct. 19, 2009

(65) Prior Publication Data

US 2010/0063152 A1     Mar. 11, 2010

Related U.S. Application Data

(63) Continuation-in-part of application No. 12/402,484, filed on Mar. 11, 2009.

(60) Provisional application No. 61/035,706, filed on Mar. 11, 2008.

(51) Int. Cl.

| | |
|---|---|
| *A61K 31/10* | (2006.01) |
| *A61K 31/195* | (2006.01) |
| *A61K 45/06* | (2006.01) |
| *A61K 47/20* | (2006.01) |
| *A61K 9/00* | (2006.01) |

(52) U.S. Cl.
CPC ............ *A61K 47/20* (2013.01); *A61K 9/0014* (2013.01); *A61K 31/10* (2013.01); *A61K 31/195* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 3,966,924 | A * | 6/1976 | Fredriksson | 514/171 |
| 6,288,026 | B1 * | 9/2001 | Exner | A61K 9/0019 424/184.1 |
| 6,579,543 | B1 * | 6/2003 | McClung | 424/728 |
| 2006/0172972 | A1 * | 8/2006 | Bhushan et al. | 514/79 |
| 2006/0177430 | A1 * | 8/2006 | Bhushan et al. | 424/94.1 |
| 2007/0021505 | A1 * | 1/2007 | Bhushan et al. | 514/553 |
| 2008/0038219 | A1 * | 2/2008 | Mosbaugh et al. | 424/74 |

FOREIGN PATENT DOCUMENTS

| | | | |
|---|---|---|---|
| EP | 1676570 A1 | * | 7/2006 |
| WO | WO 9100728 A1 | * | 1/1991 |
| WO | WO 9405272 A1 | * | 3/1994 |
| WO | WO 9739746 A1 | * | 10/1997 |
| WO | WO2007/011874 A2 | * | 1/2007 |
| WO | WO 2009063485 A2 | * | 5/2009 |

OTHER PUBLICATIONS

Helander et al. (Acta Derm Venereol., vol. 67, No. 6, abstract; 1987).*
Nisenson (The Journal of Pediatrics, vol. 46, Issue 5, abstract; 1955).*
Lippmann et al. (Arch Phys Med Rehabil, vol. 75, No. 4, abstract; 1994).*
Nagai, The inhibition of inflammation by the promotion of spontaneous healing with L-carnosine, Langenbecks Arch Chir. 1980;351(1):39-49, printed from http://www.ncbi.nlm.nih.gov/pubmed/7401821, Abstract only, 1 page.*
Eichbaum et al., Anti-inflammatory effect of warfarin and vitamin K1, Naunyn Schmiedebergs Arch Pharmacol. Jun. 1979; 307(2):185-90, printed from http://www.ncbi.nlm.nih.gov/pubmed/573373, Abstract only, 1 page.*
Healthyl Protocols—Chelation Protocol, Sep. 30, 2009, printed from http://web.archive.org/web/20090930055015/http://healthyprotocols.com/2_chelation.htm, 7 pages.*
Vos et al., L-arginine supplementation improves function and reduces inflammation in renal allografts, J Am Soc Nephrol. Feb. 2001;12(2):361-7, printed from http://www.ncbi.nlm.nih.gov/pubmed/11158227, Abstract only, 1 page.*
Lotioncrafter.com, Lotioncrafter Disodium EDTA, May 18, 2005, printed from http://web.archive.org/web/20050518013447/http://lotioncrafter.com/reference/tech_data_edta.pdf, 2 pages.*

* cited by examiner

*Primary Examiner* — Gigi Huang
(74) *Attorney, Agent, or Firm* — Shantanu Basu; Eckman Basu LLP

(57) ABSTRACT

Methods and formulations are provided for the treatment of localized edema, particularly localized edema resulting from chronic venous insufficiency. A metal ion sequestrant is topically administered to a subject afflicted with localized edema in combination with a permeation enhancer selected from methylsulfonylmethane and a combination of methylsulfonylmethane and dimethylsulfoxide. Topically administrable formulations for use in the aforementioned method are also provided.

4 Claims, No Drawings

METHOD AND TOPICAL FORMULATION FOR TREATING LOCALIZED EDEMA

CROSS-REFERENCE TO RELATED APPLICATIONS

This application is a continuation-in-part of U.S. Ser. No. 12/402,484, filed Mar. 11, 2009, which claims priority under 35 U.S.C. §119(e)(1) to provisional U.S. Patent Application Ser. No. 61/035,706, filed Mar. 11, 2008. These applications are incorporated by reference herein in their entireties.

TECHNICAL FIELD

This invention relates generally to the treatment of edema, and more particularly relates to methods for the treatment of edema, e.g., lower leg edema, using a topically applied formulation and to formulations useful in that method.

BACKGROUND

Inflammation is a complex biological response of vascular tissue to harmful stimuli, such as oxidative stress, irritants, pathogens, and damaged cells. It is a protective attempt by the organism to remove an injurious stimulus and initiate the healing process for injured tissue. The inflammatory response involves the production and release of inflammatory modulators that function to both destroy damaged cells and heal injured tissue. In order to perform this function, however, various inflammatory modulators either directly produce and/or signal the release of agents that produce reactive oxygen species for the purpose of destroying invading agents and/or injured cells. The inflammatory response, therefore, involves a balance between the destruction of damaged cells and the healing of injured tissue, since an imbalance can lead to oxidative stress and the onset of various inflammatory disease pathologies.

One manifestation of the inflammatory process in the body is edema, the term "edema" referring to the accumulation of excess fluid within body tissues. Not all edema, however, has been established as caused by or associated with inflammation. Edema may be systemic in nature (as in congestive heart failure, renal failure, or pulmonary edema) or localized. Localized edema generally involves swelling of the arms or legs, with lower leg edema particularly common. The effects of localized edema are well known. Patients can be somewhat to significantly disabled, as a substantial volume of fluid can accumulate in the affected limb or limbs. Normal, everyday activities can become severely limited. Elderly people are particularly susceptible to development of localized edema, since the elderly frequently suffer from medical conditions in which blood flow is limited or decreased, and/or take medications that can give rise to edema. The most common reason for edema in many people is chronic venous insufficiency.

Although treatment of the underlying pathology, if such treatment is possible, will normally reduce edemic swelling, treatment is often unavailable or only partially effective. Lymphedema, for example, is a chronic condition that cannot be cured. One solution that is used in alleviating edema, particularly in the management of lymphedema, is compression therapy. That is, the swollen limb is wrapped and compressed to reduce and/or disseminate the localized, accumulated fluid. For example, the ReidSleeve® (Peninsula Medical, Inc.) is a compression device formed of a flexible synthetic material which is strapped on to a patient's limb at the site of swelling and then tightened (see U.S. Pat. Nos. 5,904,145, 5,916,183, and 5,196,231 to Reid). See also U.S. Pat. No. 5,759,164 to Pacey and U.S. Pat. No. 5,830,164 to Cone et al., both of which also describe devices for applying pressure to an edemic limb. The use of such compression bandaging has provided some beneficial results to patients, but is potentially harmful unless the amount of pressure applied is carefully controlled and regularly monitored. Otherwise, application of significant pressure can exacerbate the patient's condition or cause additional problems, by excessively reducing or even blocking blood circulation. While these types of devices can be safely and effectively applied by the medical practitioner, once the patient is home and applying the compression sleeve without guidance, its use becomes risky.

Pharmacological agents have also been proposed for use in treating localized edema; such agents are typically selected from those drugs normally used in the treatment of generalized inflammation, e.g., NSAIDs such as aspirin, ibuprofen, and the like, corticosteroids, and antihistamines. These agents can provide some degree of improvement, but relief is often minimal and short-lived. There are no known treatments that provide significant and lasting relief from localized edema.

SUMMARY OF THE INVENTION

In one aspect of the invention, a method is provided for treating a patient afflicted with localized edema. Generally, although not necessarily, the edema results from chronic venous insufficiency, and the edema may or may not be associated with or caused by an inflammatory condition, e.g., an inflammatory response or inflammatory disease. The method involves topically administering to the patient a therapeutically effective amount of a metal ion sequestering agent (also referred to herein as a "metal ion sequestrant" or simply as a "sequestrant") and an effective permeation-enhancing amount of a permeation enhancer, e.g., methylsulfonylmethane. "Topically" administering the formulation, as that term is used herein, means that the formulation is applied to the body surface, typically the skin. The sequestrant is capable of sequestering, e.g., chelating or otherwise sequestering metal ions, including metal ions that may be directly or indirectly causing the condition responsible for the edema. The permeation enhancer acts to increase the rate at which the metal ion sequestrant penetrates the body surface and therefore also increases the amount of sequestrant that is delivered, relative to the rate and amount that would be observed in the absence of the permeation enhancer.

The sequestrant and the enhancer are generally, although not necessarily, administered in a single formulation in which the two components are combined, e.g., a cream, lotion, gel, or the like. The method may, however, also involve separate administration of the sequestrant and enhancer.

In another aspect of the invention, a topical formulation is provided for the treatment of localized edema. The formulation contains a therapeutically effective amount of a metal ion sequestrant and an effective permeation-enhancing amount of a permeation enhancer as described above. By an "effective amount" of each of the foregoing components is meant that when a dose, e.g., a unit dose, of the formulation is topically applied, the concentration of the sequestrant provides a therapeutically effective amount of the sequestrant and the concentration of the permeation enhancer provides an effective permeation-enhancing amount. The formulation also contains a pharmaceutically acceptable topical carrier including one or more inert additives, i.e., excipients, as will be explained infra. Optionally, when used to treat localized edema resulting from inflammation, the topical formulation may also contain an anti-inflammatory agent.

Other features and advantages of the disclosure will be apparent from the following detailed description and claims.

DETAILED DESCRIPTION OF THE INVENTION

Definitions and Terminology:

It is to be understood that unless otherwise indicated this disclosure is not limited to particular embodiments described, as such may vary. It is also to be understood that the terminology used herein is for the purpose of describing particular embodiments only, and is not intended to be limiting. Unless defined otherwise, all technical and scientific terms used herein have the same meaning as commonly understood by one skilled in the art to which this disclosure belongs.

As used herein and in the appended claims, the singular forms "a", "and", and "the" include plural referents unless the context clearly dictates otherwise. Thus, for example, "a metal ion sequestrant" encompasses a plurality of metal ion sequestrants as well as a single sequestrant, and reference to permeation enhancer includes reference to two or more permeation enhancers as well as a single enhancer.

In this specification and in the claims that follow, reference will be made to a number of terms, which shall be defined to have the following meanings:

"Optional" or "optionally present"—as in an "optional additive" or an "optionally present additive"—means that the subsequently described component (e.g., additive or anti-inflammatory agent) may or may not be present, so that the description includes instances where the component is present and instances where it is not.

By "pharmaceutically acceptable" is meant a material that is not biologically or otherwise undesirable, e.g., the material may be incorporated into a formulation of the invention without causing substantial side effects or interacting in a deleterious manner with any of the other components of the formulation. When the term "pharmaceutically acceptable" is used to refer to a pharmaceutical excipient, it is implied that the excipient has met the required standards of toxicological and manufacturing testing and/or that it is included on the Inactive Ingredient Guide prepared by the U.S. Food and Drug Administration. As explained in further detail infra, "pharmacologically active" (or simply "active") as in a "pharmacologically active" derivative or analog refers to a derivative or analog having the same type of pharmacological activity as the parent agent.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of an undesirable condition or damage. Thus, for example, "treating" a subject according to the present method involves prevention of localized edema in a susceptible individual as well as treatment of a clinically symptomatic individual.

The term "active agent" or "pharmacologically active agent" refers to a chemical compound, complex or composition that exhibits a desirable effect in the biological context, i.e., when administered to a subject. The term includes pharmacologically active, pharmaceutically acceptable derivatives of those active agents specifically mentioned herein, including, but not limited to, salts, esters, amides, prodrugs, active metabolites, isomers, analogs, crystalline forms, hydrates, and the like. When the term "active agent" is used, or when a particular active agent is specifically identified (e.g., a specific anti-inflammatory agent suitable for topical administration), then, it is to be understood that pharmacologically active, pharmaceutically acceptable salts, esters, amides, prodrugs, active metabolites, isomers, analogs, etc. of the agent are intended as well as the agent per se.

"Carriers" as used herein refer to conventional pharmaceutically acceptable, pharmacologically inactive carrier and excipient materials suitable for topical drug administration, and include any such materials known in the art that are nontoxic and do not interact with other components of the pharmaceutical formulation in a deleterious manner. The term "carriers" is intended to encompass all pharmaceutically acceptable, pharmacologically inactive materials that may be referred to in the art as additives, excipients, vehicles, auxiliary agents, and the like.

The terms "patient" and "subject" as used herein refer to a mammalian being, generally a human being.

The term "about" as used herein may be applied to modify any quantitative representation that could permissively vary without resulting in a change in the basic function to which it is related.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Unless otherwise indicated, the invention is not limited to specific formulation components, active agents, dosage regimens, or the like, as such may vary.

Indication, Treatment, and Topical Formulations:

The present invention provides methods and formulations for the treatment of a subject with localized edema, which generally, although not necessarily, is caused by chronic venous insufficiency. The edema may or may not be caused by or associated with inflammation. As noted above, "treatment" of the localized edema encompasses prevention of localized edema in a susceptible individual as well as treatment of a clinically symptomatic individual.

In one embodiment, a method of treating localized edema in a patient involves topical administration, at the site of the edema, of (1) a therapeutically effective amount of a metal ion sequestrant, e.g., a chelating agent, and (2) an effective permeation-enhancing amount of a permeation enhancer. The metal ion sequestrant is capable of sequestering metal ions that are associated in some way with a dysfunctional process, typically a dysfunctional inflammatory process. For instance, metal ions such as $Fe^{2+}$ and $Fe^{3+}$ may act as catalysts in oxidative reactions in the extracellular milieu, thereby reducing the availability of such reactive metal ions for participating in the production of reactive oxygen species. An elevated concentration of calcium cation, $Ca^{2+}$, is associated with oxidative stress, i.e., an increase in the production of reactive oxygen species, which can in turn lead to a number of physiological problems.

The aforementioned method will generally, although not necessarily, involve topical administration of the metal ion sequestrant and the enhancer in a single formulation, e.g., a cream, lotion, gel, or the like.

The permeation enhancer is essentially a transport enhancing agent, i.e., the enhancer facilitates transport of the sequestrant and any pharmacologically active agent present (e.g., an anti-inflammatory agent) into and through the body surface and into body tissues and membranes, e.g., into and through phospholipid membranes, into cells, and, in certain instances, into the organelles thereof, such as the nucleus and/or mitochondria. The "permeation-enhancing amount" of the enhancer refers to an amount that is effective (1) to increase the rate of permeation of a formulation component, particularly the sequestrant and any active agent present, through the body surface and into the underlying tissues, and/or (2) to increase the amount of a formulation component, particularly the sequestrant and any active agent present, that penetrates through the body surface and into the underlying tissues.

Generally, the metal ion sequestrants can be divided into two categories, chelators and complexing ligands.

The word chelator comes from the Greek word "chele" which means "claw" or "pincer." As the name implies, metals that are complexed with chelators form a claw-like structure consisting of one or more molecules. The metal chelate structure may be circular, and may include 5 or 6 member rings that are structurally and chemically stable.

Chelators can be classified by two different methods. One method is by their use: they may be classified as extraction type and color-forming type. Extractions with chelators may be for preparative or analytical purposes. The chelating extraction reaction generally consists of addition of a chelator to a metal-containing solution or material to selectively extract the metal or metals of interest. The color-forming type of chelators—including pyridylazonaphthol (PAN), pyridylazoresorcinol (PAR), thioazoylazoresorcinol (TAR), and many others—have been used in analytical chemistry for many years. The chemistry is similar to that of the extraction type, except that the color-forming chelator will form a distinctive color in the presence or absence of a targeted metal. Generally the types of functional groups that form the chelate complex are similar; however, a color-forming chelator will be water soluble due to the addition of polar or ionic functional groups (such as a sulfonic acid group) to the chelating molecule.

Another method of classifying chelators is according to whether or not the formation of the metal chelate complex results in charge neutralization. Chelators often contain hydronium ions (from a carboxylic acid or hydroxy functional group) that result in charge neutralization, e.g., 8-hydroxyquinoline. Other chelators are non-ionic and simply bind to the metal, thereby conserving the charge of the metal, e.g., ethylene diamine or 1,10-phenanthroline. Chelators sometimes have one acidic group and one basic group which, upon chelation with the metal ion, form a ring structure. Typical acidic groups are carboxylic acid (—COOH), hydroxyl (OH; phenolic or enolic), sulfhydryl (—SH), hydroxylamino (—NH—OH), and arsonic acid (—AsO(OH)$_2$). Typical basic groups include oxo (=O) and primary, secondary, and tertiary amine groups. Virtually all organic functional groups have been incorporated into chelators.

A complexing ligand may not form a ring structure, but may still be able to form strong complexes with the metal atom. An example of a complexing ligand is cyanide, which can form strong complexes with certain metals such as $Fe^{3+}$ and $Cu^{2+}$. Free cyanide is used to complex and extract gold metal from ore. One or more of the ligands can complex with the metals depending on the ligand and ligand concentration.

It is possible to add selectivity to the complexation reaction. Some metal ion sequestrants are very selective for a particular metal. For example, dimethylglyoxime forms a planar structure with $Ni^{2+}$ and selectively extracts the metal. Selectivity can be moderated by adjusting the pH. When an acidic group is present, the chelator is made more general by increasing pH and more selective by decreasing the pH. Only metals that form the strongest chelators will form metal chelates under increasingly acidic conditions. As another example, BAPTA selectively chelates calcium ions, EGTA chelates both calcium ions and magnesium ions but is more selective for calcium ions, and EDTA chelates both iron and calcium ions as well as other dicationic and tricationic metal species.

Chelating or ligand complexers may be used in conjunction with other metal chelators to add selectivity. Masking agents are used as an auxiliary complexing agent to prevent the complexation of certain metals so that others can be complexed. Examples of masking agents include sulfosalicylate which masks $Al^{3+}$, cyanide which masks $Co^{2+}$, $Ni^{2+}$, $Cu^{2+}$, $Cd^{2+}$ and $Zn^{2+}$, thiourea which masks $Cu^{2+}$, citrate which masks $Al^{3+}$, $Sn^{4+}$ and $Zr^{4+}$, and iodide which masks $Hg^{2+}$.

Table 1 indicates some of the more common metal complexers and some of the cations with which they form complexes. In the table, the abbreviations used in the category headings are as follows: E, extraction; CF, color forming; CN, charge neutralizing; and NCN, no charge neutralization.

TABLE 1

| Complexer | E | CF | CN | NCN | Representative ions complexed |
|---|---|---|---|---|---|
| 2-Aminoperimidine hydrochloride | x | | | x | $SO_4^{2-}$, $Ba^{2+}$ |
| 1-Phenyl-3-methyl-4-benzoylpyrazolin-5-one | x | | | x | $Pu^{4+}$, $UO_2^{2+}$ |
| Eriochrome black T | | x | x | | $Ca^{2+}$, $Mg^{2+}$, Sr, Zn, Pb |
| Calmagite | | x | x | | $Ca^{2+}$, $Mg^{2+}$, Sr, Zn, Pb |
| o,o-Dihydroxyazobenzene | | x | x | | $Ca^{2+}$, $Mg^{2+}$ |
| Pyridylazonaphthol (PAN) | | x | x | | Bi, Cd, Cu, Pd, Pl, $Sn^{2+}$, $UO_2^{2+}$, $Hg^{2+}$, Th, Co, Pb, $Fe^{2+}$, $Fe^{3+}$, $Ni^{2+}$, $Zn^{2+}$, $La^{+3}$ |
| Pyridylazonaphthol (PAN) | x | | x | | Alkali metals, $Zr^{4+}$, Ge, Ru, Rh, Ir, Be, Os |
| Pyridylazo-resorcinol (PAR) | | x | x | | $ReO_4^-$, Bi, Cd, Cu, Pd, Pl, $Sn^{2+}$, $UO_2^{2+}$, $Hg^{2+}$, Th, Co, Pb, $Fe^{2+}$, $Fe^{3+}$, $Ni^{2+}$, $Zn^{2+}$, $La^{3+}$ |
| Thiazolylazo resorcinol (TAR) | | x | x | | Pb |
| 1,10-Phenanthroline | x | | | x | $Fe^{2+}$, Zn, Co, Cu, Cd, $SO_4^{2-}$ |
| 2,2'-Bipyridine | x | | | x | |

TABLE 1-continued

| Complexer | E | CF | CN | NCN | Representative ions complexed |
|---|---|---|---|---|---|
| Tripyridine | | | x | x | |
| Bathophenanthroline (4,7-diphenyl-1,10-phenanthroline) | | | | x | $Cu^{2+}$, $Cu^+$, $Fe^{2+}$ |
| Bathophenanthroline (4,7 diphenyl-2,9-dimethyl-1,10-phenanthroline) | | | x | x | $Cu^{2+}$, $Cu^+$, $Fe^{2+}$ |
| Cuproine | | | x | x | $Cu^{2+}$, $Cu^+$, $Fe^{2+}$ |
| Neocuproine | | | x | x | $Cu^{2+}$, $Cu^+$, $Fe^{2+}$ |
| 2,4,6-Tripyridyl-S-triazine | | | x | | $Fe^{2+}$ |
| Phenyl-2-pyridyl ketoxime | | | x | | $Fe^{2+}$ |
| Ketoxime | | x | | | |
| Ferrozine | | | x | x | $Fe^{2+}$ |
| Bicinchoninic acid | | | | x | $Cu^{2+}$, $Cu^+$ |
| 8-Hydroxyquinoline | x | | x | | Pb, $Mg^{2+}$, $Al^{3+}$, Cu, Zn, Cd |
| 2-Amino-6-sulfo-8-hydroxyquinoline | x | | x | | |
| 2-Methyl-8-hydroxyquinoline | x | | x | | Pb, $Mg^{2+}$, Cu, Zn, Cd |
| 5,7-Dichloro 8-hydroxyquinoline | x | | x | | Pb, $Mg^{2+}$, $Al^{3+}$, Cu, Zn, Cd |
| Dibromo-8-hydroxyquinoline | x | | x | | Pb, $Mg^{2+}$, $Al^{3+}$, Cu, Zn, Cd |
| Naphthyl azoxine | | x | x | | |
| Xylenol orange | | | x | x | $Th^{4+}$, $Zr^{4+}$, $Bi^{3+}$, $Fe^{3+}$, $Pb^{2+}$, $Zn^{2+}$, $Cu^{2+}$, rare earth metals |
| Calcein (Fluorescein-methylene-iminodiacetic acid) | | | x | x | $Ca^{2+}$, $Mg^{2+}$ |
| Pyrocatechol violet | | | x | x | $Sn^{4+}$, $Zr^{4+}$, $Th^{4+}$, $UO_2^{2+}$, $Y^{3+}$, $Cd^{2+}$ |
| Tiron (4,5-Dihydroxy-m-benzenedisulfonic acid) | | | x | x | $Al^{3+}$ |
| Alizarin Red S (3,4-dihydroxy-2-anthraquinonesulfonic acid) | | | x | x | $Ca^{2+}$ |
| 4-Aminopyridine | x | | | x | |
| Thoron I | | | x | | |
| Arsenazo I | | | x | x | $Ca^{2+}$, $Mg^{2+}$, $Th^{4+}$, $UO_2^{2+}$, $Pu^{4+}$ |
| Arsenazo III | | | x | x | $Ca^{2+}$, $Mg^{2+}$, $Th^{4+}$, $UO_2^{2+}$, $Pu^{4+}$, $Zr^{4+}$, $Th^{4+}$ |
| EDTA (ethylenediamine tetraacetic acid) | x | | x | | $Fe^{2+}$, most divalent cations |
| CDTA (cyclodiamine tetracetic acid) | x | | x | | $Fe^{2+}$, most divalent cations |
| EGTA (ethylene glycol bis (β-aminoethylether)-N,N,N',N'-tetraacetic acid) | x | | x | | $Fe^{2+}$, most divalent cations |
| HEDTA (hydroxyethyl-ethylenediamine triacetic acid) | | | x | | $Fe^{2+}$, most divalent cations |
| DPTA (diethylenetriamine pentaacetic acid) | x | | x | | $Fe^{2+}$, most divalent cations |
| DMPS (dimercaptopropane sulfonic acid) | x | | x | | $Fe^{2+}$, most divalent cations |
| DMSA (dimercaptosuccinic acid) | x | | x | | $Fe^{2+}$, most divalent cations |
| ATPA (aminotrimethylene phosphonic acid) | x | | x | | $Fe^{2+}$, most divalent cations |
| CHX-DTPA (Cyclohexyl diethylenetriaminopentaacetate) | x | | x | | $Fe^{2+}$, most divalent cations |
| Citric acid | x | | x | | $Fe^{2+}$ |
| 1,2-bis-(2-amino-5-fluorophenoxy)ethane-N,N,N',N'-tetraacetic acid (5F-BAPTA) | | x | x | | $Ca^{2+}$, $K^+$ |
| Desferoxamine | | | | | $Fe^{2+}$ |
| Hydroquinone | x | | x | | $Fe^{2+}$ |
| Benzoquinone | x | | x | | $Fe^{2+}$ |
| dipicrylamine | x | | x | | $K^+$ |
| Sodium tetraphenylboron | x | | x | | $K^+$ |
| 1,2-dioximes | x | | x | | $Ni^{2+}$, $Pd^{2+}$, $Mn^{2+}$, $Fe^{2+}$, $Co^{2+}$, $Ni^{2+}$, $Cu^{2+}$, $Zn^{2+}$ |
| Alpha-furil dioxime | x | | x | | $Ni^{2+}$, $Pd^{2+}$, $Mn^{2+}$, $Fe^{2+}$, $Co^{2+}$, $Ni^{2+}$, $Cu^{2+}$, $Zn^{2+}$ |
| Cyclohexanone oxime | x | | x | | $Ni^{2+}$, $Pd^{2+}$, $Mn^{2+}$, $Fe^{2+}$, $Co^{2+}$, $Ni^{2+}$, $Cu^{2+}$, $Zn^{2+}$ |
| Cycloheptanone | x | | x | | $Ni^{2+}$, $Pd^{2+}$, $Mn^{2+}$, $Fe^{2+}$, $Co^{2+}$, $Ni^{2+}$, $Cu^{2+}$, $Zn^{2+}$ |
| Methyl cyclohexanonedioxime | | | x | x | $Ni^{2+}$, $Pd^{2+}$, $Mn^{2+}$, $Fe^{2+}$, $Co^{2+}$, $Ni^{2+}$, $Cu^{2+}$, $Zn^{2+}$ |
| Ethyl cyclohexanonedioxime | | | x | x | $Ni^{2+}$, $Pd^{2+}$, $Mn^{2+}$, $Fe^{2+}$, $Co^{2+}$, $Ni^{2+}$, $Cu^{2+}$, $Zn^{2+}$ |
| Isopropyl 4-cyclohexanone- | | | x | x | $Ni^{2+}$, $Pd^{2+}$, $Mn^{2+}$, $Fe^{2+}$, $Co^{2+}$, |

TABLE 1-continued

| Complexer | E | CF | CN | NCN | Representative ions complexed |
|---|---|---|---|---|---|
| dioxime | | | | | $Ni^{2+}$, $Cu^{2+}$, $Zn^{2+}$ |
| Cupferron | x | | x | | $M^{4+}$, $M^{5+}$, $M^{6+}$, $Zr^{4+}$, $Ga^{3+}$, $Fe^{3+}$, $Ti^{4+}$, $Hf^{4+}$, $U^{4+}$, $Sn^{4+}$, $Nb^{5+}$, $Ta^{5+}$, $V^{5+}$, $Mo^{6+}$, $W^{6+}$, $Th^{4+}$, $Cu^{2+}$, $Bi^{3+}$ |
| N-Benzolyphenylhydroxyl-amine (BPHA) | | | x | | $Sn^{4+}$, $Zr^{4+}$, $Ti^{4+}$, $Hf^{4+}$, $Nb^{5+}$, $Ta^{5+}$, $V^{5+}$, $Mo^{6+}$, $Sb^{5+}$ |
| Arsonic acids | x | | x | | $Zr^{4+}$, $Ti^{4+}$ |
| Mandelic acid | x | | x | | $Zr^{4+}$, $Hf^{4+}$ |
| Alpha-nitroso-beta-napthol | x | | x | | $Co^{2+}$, $Co^{3+}$ |
| Anthranilic acid | x | | x | | $Ni^{2+}$, $Pb^{2+}$, Co, $Ni^{2+}$, $Cu^{2+}$, $Zn^{2+}$, Cd, $Hg^{2+}$, $Ag^{+}$ |
| Alpha-benzoinoxime | x | | x | | $Cu^{2+}$ |
| Thionalide | x | | x | | $Cu^{2+}$, $Bi^{3+}$, Hg, As, $Sn^{4+}$, $Sb^{5+}$, $Ag^{+}$ |
| Tannin | x | | x | | Nb, Ta |
| Ammonium oxalate | x | | x | | $Th^{4+}$, $Al^{3+}$, Cr, $Fe^{2+}$, $V^{5+}$, $Zr^{4+}$, $U^{4+}$ |
| Diethyldithio-carbamates | x | | x | | $K^{+}$, most metals |
| 2-Furoic acid | x | | x | | $Th^{4+}$ |
| Dimethylglyoxime (DMG) | x | | x | | $Ni^{2+}$, $Fe^{2+}$, $Co^{2+}$, $Al^{3+}$ |
| Isooctylthioglycolic acid | x | | x | | $Al^{3+}$, $Fe^{2+}$, $Cu^{2+}$, $Bi^{3+}$, $Sn^{4+}$, $Pb^{2+}$, $Ag^{+}$, $Hg^{2+}$ |

The listing of cations in this table should not be taken to be exclusive. Many of these sequestrants will complex to some extent with many metal cations.

Compounds useful as metal ion sequestrants herein include any compounds that coordinate to or form complexes with a divalent or polyvalent metal cation, although sequestration of calcium and iron cations is typically preferred. Preferred metal ion sequestrants herein are basic addition salts of a polyacid, e.g., a polycarboxylic acid, a polysulfonic acid, or a polyphosphonic acid, with polycarboxylates particularly preferred.

With respect to suitable sequestrants, chelators, ligands, and other species that act as iron sequestrants, for example, include the siderophores desferrioxamine (deferoxamine, DFO, desferrioxamine B, Desferal) and desferrithiocin; desferri-exochelin; 4-[3,5-bis-(hydroxyphenyl)-1,2,4-triazol-1-yl]-benzoic acid (ICL670A); 4'-hydroxydesazadesferrithiocin (4,5-dihydro-2-(2,4-dihydroxyphenyl)-4-methylthiazole-4-carboxylic acid; deferitrin); deferiprone (1,2-dimethyl-3-hydroxypyridin-4-one); hydroxypyridinone analogs; aroylhydrazones such as pyridoxal isonicotinoyl hydrazone and analogs thereof, e.g., 2-pyridylcarboxaldehyde isonicotinoyl hydrazone and its analogs, and di-2-pyridylketone isonicotinoyl hydrazone and its analogs; thiosemicarbazones such as triapine (3-aminopyridine-2-carboxaldehyde thiosemicarbazone); the polyamino carboxylic acid ethylenediamine tetraacetic acid (EDTA) and salts thereof; N,N'-di(2-hydroxybenzyl)ethylenediamine-N,N'-diacetic acid HCl (HBED); deferasirox; hydroxamic acid analogs such as 4-aminophenylhydroxamic acid, 2-aminophenylhydroxamic acid, and salicylhydroxamic acid; rhodotorulic acid; N,N'-bis(2-hydroxybenzyl)prop-ylene-1,3-diamine-N,N'-diacetic acid (HBPD), 2,3-dihydroxybenzoic acid; and diethyltriamine pentaacetic acid (DTPA).

Examples of chelators, ligands, and other species that act as calcium sequestrants include, without limitation, the polyamino carboxylic acids EDTA, ethylene glycol tetraacetic acid (EGTA), 1,2-bis(o-aminophenoxy)ethane-N,N,N',N'-tetraacetic acid) (BAPTA); and the esterified BAPTA analog 1,2-bis-(o-aminophenoxy)-ethane-N,N,N',N'-tetraacetic acid, tetraacetoxymethyl ester (BAPTA-AM).

Suitable metal ion sequestrants include monomeric polyacids such as EDTA, EGTA, BAPTA, cyclohexanediamine tetraacetic acid (CDTA), hydroxyethyl-ethylenediamine triacetic acid (HEDTA), diethylenetriamine pentaacetic acid (DTPA), dimercaptopropane sulfonic acid (DMPS), dimercaptosuccinic acid (DMSA), aminotrimethylene phosphonic acid (ATPA), citric acid, pharmacologically acceptable salts thereof, and combinations of any of the foregoing. Other exemplary metal ion sequestrants include: phosphates, e.g., pyrophosphates, tripolyphosphates, and hexametaphosphates; chelating antibiotics such as chloroquine and tetracycline; nitrogen-containing chelating agents containing two or more chelating nitrogen atoms within an imino group or in an aromatic ring (e.g., diimines, 2,2'-bipyridines, etc.); and polyamines such as cyclam (1,4,7,11-tetraazacyclotetradecane), N—(C1-C30 alkyl)-substituted cyclams (e.g., hexadecyclam, tetramethylhexadecylcyclam), diethylenetriamine (DETA), spermine, diethylnorspermine (DENSPM), diethylhomo-spermine (DEHOP), deferoxamine (N'-[5-[[4-[[5-(acetylhydroxyamino)pentyl]amino]-1,4-dioxobutyl]hydroxyamino]pentyl]-N'-(5-aminopentyl)-N-hydroxybutanediamide; also known as desferrioxamine B and DFO), deferiprone, pyridoxal isonicotinoyl hydrazone (PIH), salicylaldehyde isonicotinoyl hydrazone (SIH), ethane-1,2-bis(N-1-amino-3-ethylbutyl-3-thiol).

Additional metal ion sequestrant that may be useful for the practice of the current disclosure include EDTA-4-aminoquinoline conjugates such as ([2-(bis-ethoxycarbonyl-methyl-amino)-ethyl]-{[2-(7-chloro-quinolin-4-ylamino)-ethylcarbamoyl]-methyl}-amino)-acetic acid ethyl ester, ([2-(bis-ethoxycarbonylmethyl-amino)-propyl]-{[2-(7-chloro-quinolin-4-ylamino)-ethylcarbamoyl]-methyl}-amino)-acetic acid ethyl ester, ([3-(bis-ethoxycarbonylm-ethyl-amino)-propyl]-{[2-(7-chloro-quinolin-4-ylamino)-ethylcarbamoyl]-methyl}-amino)-acetic acid ethyl ester, ([4-(bis-ethoxycarbonylmethyl-amino)-butyl]-{[2-(7-chloro-quinolin-4-ylamino)-ethylcarbamoyl]-methyl}-amino)-acetic acid ethyl ester, ([2-(bis-ethoxymethyl-amino)-ethyl]-{[2-(7-chloro-quinolin-4-ylamino)-ethylcarbamoyl]-methyl}-amino)-acetic acid ethyl ester, ([2-(bis-ethoxymethyl-amino)-propyl]-{[2-(7-chloro-quino-lin-4-ylamino)-ethylcarbamoyl]-methyl}-amino)-acetic acid ethyl ester, ([3-(bis-ethoxymethyl-amino)-propyl]-{[2-(7- chloro-quinolin-4-ylamino)-ethylcarbamoyl]-methyl}-amino)-acetic acid ethyl ester, ([4-(bis-ethoxymethyl-amino)-butyl]-{[2-(7-chloro-quinolin-4-ylamino)-ethylcarbamoyl]-methyl}-amino)-acetic acid ethyl ester, as described in Solomon et al. (2006) *Med. Chem.* 2: 133-138.

The metal ion sequestrant is included in the topical formulations herein in a therapeutically effective amount, i.e., at a concentration that provides a therapeutically effective amount when a single dose of the formulation is administered topically. Generally, the concentration of the sequestrant is in the range of about 0.6 wt. % to about 10 wt. %, for instance, about 1.0 wt. % to about 5.0 wt. %.

The disclosure is not, unless otherwise indicated, limited with regard to specific metal ion sequestrants, and any such agents can be used providing, in general, that they are capable of being buffered to a pH in the range of about 6.5 to about 8.0 and does not interact with any other component of the formulation. EDTA and pharmacologically acceptable EDTA salts may be advantageously used. Representative pharmacologically acceptable EDTA salts are typically selected from diammonium EDTA, disodium EDTA, dipotassium EDTA, triammonium EDTA, trisodium EDTA, tripotassium EDTA, and calcium disodium EDTA. EDTA has been widely used as an agent for chelating metals in biological tissue and blood. For example, U.S. Pat. No. 6,348,508 to Denick Jr. et al. describes EDTA as a sequestrant to bind metal ions. In addition to its use as a chelating agent, EDTA has also been widely used as a preservative in place of benzalkonium chloride, as described, for example, in U.S. Pat. No. 6,211,238 to Castillo et al. U.S. Pat. No. 6,265,444 to Bowman et al. discloses use of EDTA as a preservative and stabilizer.

With respect to the enhancer, the compound or compounds used should be present in an effective permeation-enhancing amount wherein the "effective permeation-enhancing amount" of the enhancer generally represents a concentration that is sufficient to provide a measurable increase in the rate of permeation of one or more formulation components, e.g., the sequestrant, through the body surface and into underlying tissues, and/or an increase in the amount of a formulation component, e.g., the sequestrant, that permeates through the body surface and into underlying tissues. The "increase" in the rate of permeation and/or amount permeated represents an increase relative to that which would be observed in the absence of the enhancer.

The invention is not limited with respect to the mechanism by which the enhancer increases permeation of formulation components through the patient's body surface penetration into underlying tissues. The enhancer should be selected such that it enables penetration, permeation, and transport of the metal ion sequestrant as explained above. The enhancer should have minimal or no toxicity, and any degradation products should have minimal or no toxicity as well.

Suitable enhancers include, by way of example, substances having the formula:

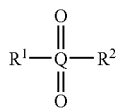

wherein $R^1$ and $R^2$ are independently selected from $C_1$-$C_6$ alkyl (preferably $C_1$-$C_3$ alkyl), $C_1$-$C_6$ heteroalkyl (preferably $C_1$-$C_3$ heteroalkyl), $C_6$-$C_{14}$ aralkyl (preferably $C_6$-$C_8$ aralkyl), and $C_2$-$C_{12}$ heteroaralkyl (preferably $C_4$-$C_{10}$ heteroaralkyl), and Q is S or P. Compounds wherein Q is S and $R^1$ and $R^2$ are $C_1$-$C_3$ alkyl are particularly preferred.

The phrase "having the formula" or "having the structure" is not intended to be limiting and is used in the same way that the term "comprising" is commonly used. With respect to the above structure, the term "alkyl" refers to a linear, branched, or cyclic saturated hydrocarbon group containing 1 to 6 carbon atoms, such as methyl, ethyl, n-propyl, isopropyl, n-butyl, isobutyl, t-butyl, cyclopentyl, cyclohexyl and the like. If not otherwise indicated, the term "alkyl" includes unsubstituted and substituted alkyl, wherein the substituents may be, for example, halo, hydroxyl, sulfhydryl, alkoxy, acyl, etc. The term "alkoxy" intends an alkyl group bound through a single, terminal ether linkage; that is, an "alkoxy" group may be represented as —O-alkyl where alkyl is as defined above. The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 14 carbon atoms. Exemplary aryl groups are contain one aromatic ring or two fused or linked aromatic rings, e.g., phenyl, naphthyl, biphenyl, diphenylether, diphenylamine, benzophenone, and the like. "Aryl" includes unsubstituted and substituted aryl, wherein the substituents may be as set forth above with respect to optionally substituted "alkyl" groups. The term "aralkyl" refers to an alkyl group with an aryl substituent, wherein "aryl" and "alkyl" are as defined above. Preferred aralkyl groups contain 6 to 14 carbon atoms, and particularly preferred aralkyl groups contain 6 to 8 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The term "acyl" refers to substituents having the formula —(CO)-alkyl, —(CO)-aryl, or —(CO)-aralkyl, wherein "alkyl," "aryl, and "aralkyl" are as defined above. The terms "heteroalkyl" and "heteroaralkyl" are used to refer to heteroatom-containing alkyl and aralkyl groups, respectively, i.e., alkyl and aralkyl groups in which one or more carbon atoms is replaced with an atom other than carbon, e.g., nitrogen, oxygen, sulfur, phosphorus or silicon, typically nitrogen, oxygen or sulfur.

Suitable enhancers include methylsulfonylmethane (MSM; also referred to as methyl sulfone, dimethyl sulfone, and $DMSO_2$) and/or combinations of MSM with dimethylsulfoxide (DMSO). MSM is an odorless, highly water-soluble (34% w/v at 79° F.) white crystalline compound with a melting point of 108-110° C. and a molecular weight of 94.1 g/mol. MSM is thought to serve as a multifunctional agent herein, insofar as the agent not only increases the permeability of biological membranes such as cell membranes, but also facilitates the transport of one or more formulation components throughout the layers of the skin (i.e., epidermis, dermis and subcutaneous fat layers), as well as across mucus membranes, endothelial layers, and the like. Furthermore, MSM per se is known to provide medicative effects, and can serve as an anti-inflammatory agent as well as an analgesic. MSM also acts to improve oxidative metabolism in biological tissues, and is a source of organic sulfur, which may assist in the reduction of scarring. MSM additionally possesses beneficial solubilization properties, in that it is soluble in water, as noted above, but exhibits both hydrophilic and hydrophobic properties because of the presence of polar S=O groups and nonpolar methyl groups. The molecular structure of MSM also allows for hydrogen bonding with other molecules, i.e., between the oxygen atom of each S=O group and hydrogen atoms of other molecules, and for formation of van der Waals associations, i.e., between the methyl groups and nonpolar (e.g., hydrocarbyl) segments of other molecules.

The present formulations may contain, in addition to the MSM or MSM/DMSO combination, one or more additional permeation enhancers. Such enhancers are known to those in the field of topical and transdermal drug delivery, and include, by way of example, alkanols such as ethanol; ethers such as diethylene glycol monoethyl ether and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80) and lecithin; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate (PEGML; see, e.g., U.S. Pat. No. 4,568,343); and amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine.

The methods and formulations herein may involve use of two or more metal ion sequestrants used in combination and/or two or more enhancers used in combination. For example, a formulation of the disclosure can contain DMSO in addition to MSM. Since MSM is a metabolite of DMSO (i.e., DMSO is enzymatically converted to MSM), incorporating DMSO into an MSM-containing formulation of the disclosure will tend to gradually increase the fraction of MSM in the formulation. DMSO may also serve as a free radical scavenger, thereby reducing the potential for oxidative damage. If DMSO is added as a secondary enhancer, the amount is preferably in the range of about 1.0 wt. % to 2.0 wt. % of the formulation, and the weight ratio of MSM to DMSO is typically in the range of about 1:1 to about 50:1.

A factor that appears to be related to the performance of the present formulations is the molar ratio of the enhancer to the metal ion sequestrant. The molar ratio of the enhancer to the sequestrant is generally in the range of about 2:1 to about 12:1. The preferred molar ratio of the enhancer to the sequestrant is in the range of about 4:1 to about 10:1, more preferably in the range of about 6:1 to about 8:1, e.g., 8:1. Generally, but preferably within the limits defined by the aforementioned molar ratio ranges, the concentration of the enhancer is on the order of a few percent by weight, for example in the range of about 1 wt. % to about 8 wt. %, typically in the range of about 2 wt. % to about 6 wt. %. For example, when the enhancer is MSM per se and the sequestrant is EDTA, a concentration of about 2.5 wt % EDTA and about 5 wt % MSM may be used.

The formulations herein may consist essentially of the metal ion sequestrant and the enhancer, such that no additional therapeutic agents are incorporated, although various excipients, carriers, preservatives, and the like will typically be present.

In an alternative embodiment, the formulation may include an added anti-inflammatory agent in a therapeutically or prophylactically effective amount (as explained elsewhere herein, the term "therapeutic" is generally intended to encompass "prophylactic" use as well).

Any suitable anti-inflammatory agent in any suitable amount may be used so long as the anti-inflammatory agent is capable of being combined with the metal ion sequestrant and/or enhancer components to provide a formulation that is capable of preventing and/or treating localized edema that is directly or indirectly caused by an underlying inflammatory condition. Thus, in this embodiment, the present invention encompasses a formulation comprising one or more metal ion sequestrants, one or more enhancers, and one or more anti-inflammatory agents. Accordingly, a suitable anti-inflammatory agent may be one or more of those described herein below.

Preferred anti-inflammatory agents herein are nonsteroidal antiinflammatory drugs (NSAIDS) including, without limitation:

salicylic acid and salicylic acid derivatives such as salicylic acid per se, acetylsalicylic acid (aspirin), methyl salicylate, aloxiprin, diflunisal, salsalate, olsalazine, and sulfasalazine;

p-aminophenol derivatives such as acetaminophen;

acetic acid derivatives such as indomethacin, sulindac, etodolac, tolmetin, zomepirac, diclofenac, alclofenac, bumadizone, lonazolac, fentiazac, acemtacin, difenpiramide, oxymetacin, proglumetacin, ketorolac, aceclofenac, and bufexamac;

fenamates (derivatives of N-phenylanthranilic acid) and analogs thereof, such as mefanamic acid, flufenamic acid, meclofenamic acid, tolfenamic acid, and meclofenamate sodium;

propionic acids such as ibuprofen, dexibuprofen, naproxen, fenoprofen, ketoprofen, dexketoprofen, benoxaprofen, indoprofen, pirprofen, carprofen, pranoprofen, alminoprofen, flunoxaprofen, vedaprofen, butibufen, fenbufen, suprofen, indoprofen, ibupiroxam, oxaprozin, flurbiprofen, tepoxalin, and tiaprofenic acid;

enolic acids, i.e., "oxicams" such as piroxicam, meloxicam, lornoxicam, cinnoxicam, droxicam, sudoxicam, and tenoxicam;

pyrazolidine derivatives and analogs such as phenylbutazone, apazone, oxyphenbutazone, mofebutazone, clofezone, kebuzone, feprazone, suxibuzone, antipyrine, aminopyrine, and dipyrone;

selective COX-2 inhibitors, including diaryl-substituted furanones, diarylsubstituted pyrazoles, indole acetic acids, and sulfonanilides, such as rofecoxib, celecoxib, parecoxib, valdecoxib, etoricoxib, lumiracoxib, firocoxib, robenacoxib, mavacoxib, and cimicoxib; and other NSAIDs including nabumetone, niflumic acid, glucosamine, and benzydamine, Other anti-inflammatory agents that can be used herein are steroidal, e.g., selected from such as hydrocortisone, hydrocortisone-21-monoesters (e.g., hydrocortisone-21-acetate, hydrocortisone-21-butyrate, hydrocortisone-21-propionate, hydrocortisone-21-valerate, etc.), hydrocortisone-17, 21-diesters (e.g., hydrocortisone-17,21-diacetate, hydrocortisone-17-acetate-21-butyrate, hydrocortisone-17, 21-dibutyrate, etc.), alclometasone, alclometasone diproprionate, amcinonide, beclomethasone, beclomethasone monopropionate, betamethasone benzoate, betamethasone diproprionate, betamethasone 17-valerate, budesonide, clobetasol, clobetasol propionate, dexamethasone, flumethasone, flunisolide, fluocinolone, fluocinonide, fluticasone propionate, halometasone, mometasone furoate, prednisolone, methylprednisolone, and triamcinolone acetonide, and triamcinolone hexacetonide.

In addition to medical drugs, including but not limited to those described above, many herbs have anti-inflammatory qualities, including hyssop, ginger, Arnica montana which contains helenalin, a sesquiterpene lactone, and willow bark, which contains salicylic acid, a substance related to the active ingredient in aspirin. These herbs are encompassed by the present disclosure and one or more herbs can be combined in a formulation with one or more chelators and one or more enhancers.

A variety of means can be used to prepare the topical formulations of the invention. Techniques for pharmaceutical formulation and administration may be found in "Remington: The Science and Practice of Pharmacy," Twentieth Edition, Lippincott Williams & Wilkins, Philadelphia, Pa. (1995). For human or animal administration, preparations should meet sterility, pyrogenicity, and general safety and purity standards comparable to those required by the FDA. Administration of the pharmaceutical formulation can be performed in a variety of ways, as described herein.

The amount of the formulation administered, the relative amounts of each component therein (e.g., metal ion sequestrant, enhancer, anti-inflammatory agent, etc.), and the dosage regimen will depend on a number of factors and will vary from subject to subject and depend on, for example, the severity of the localized edema, symptoms, the subject's age, weight and general condition, and the judgment of the prescribing physician.

The formulations of the invention are administered topically to a patient at the site of the localized edema. The term "topical administration" is used in its conventional sense to mean delivery (e.g., process of applying or spreading one or more formulations according to the instant disclosure onto the body surface) to a predetermined area of skin or mucosa of a subject, where one or more of the components of the formulation permeates through the upper layers of the body surface and into the underlying tissues. The formulation is applied to a predetermined area of skin or mucosal tissue, wherein that area is usually be in the range of about 15 $cm^2$ to about 800 $cm^2$, more usually in the range of about 20 $cm^2$ to about 700 $cm^2$, most typically in the range of about 25 $cm^2$ to about 600 $cm^2$. It will be appreciated by those skilled in the art of drug delivery, however, that the area of skin or mucosal tissue through which drug is administered may vary significantly, depending on the extent of the localized edema.

With ointments, creams, lotions, gels, etc., the concentration of each active agent in the formulation should be sufficient to enable delivery of a unit dose by application of about 0.5 g to about 30.0 g of the formulation, typically in the range of about 0.5 g to about 10.0 g of the formulation, most typically in the range of about 1.0 g to about 7.5 g of the formulation.

Suitable formulations for topical administration include lotions, creams, gels, ointments, pastes, and the like, with lotions, creams, and gels particularly preferred. Topical formulations may also be prepared with liposomes, micelles, and microspheres.

In addition to the sequestrant and the enhancer, the present formulations contain one or more pharmaceutically acceptable carriers suitable for incorporation into a topically applied composition. These auxiliary agents are pharmaceutically acceptable and may be naturally occurring or may be of synthetic origin. Such optional additives will depend on the formulation type, e.g., cream, lotion, gel, or the like, but generally include, by way of example, liquid, generally aqueous, carriers (e.g., water or a hydrogel), preservatives, thickening agents, emulsifying agents, pH buffering agents, binders, coloring agents, fragrance, and the like. Representative preservatives for use in the present compositions include butylated hydroxyanisole, butylated hydroxytoluene, chlorobutanol, ethylenediamine, ethylparaben, methylparaben, monothioglycerol, phenol, phenylethyl alcohol, propylparaben, sodium benzoate, sodium formaldehyde sulfoxylate, sodium metabisulfite, sorbic acid, sulfur dioxide, maleic acid, and propyl gallate. Thickening agents include, by way of example, sodium alginate, xanthan gum, carrageenans, acacia, agar, gum tragacanth, carboxypolymethylene, polyvinylpyrrolidone, polyacrylamide, and cellulosic polymers, particularly the more hydrophilic cellulose derivatives. Sodium alginate and xanthan gum are preferred thickening agents.

Pharmaceutical creams are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant.

Lotions are preparations that may be applied without friction, and are typically liquid or semiliquid preparations in which solid particles, including the active agent, are present in a water or alcohol base along with a suspending agent; lotions are typically emulsions of the oil-in-water type. In general, pharmaceutical emulsions are generally formed from a dispersed phase (e.g., a pharmacologically active agent), a dispersion medium, and an emulsifying agent.

A variety of means can be used to prepare the topical formulations of the invention. Techniques for pharmaceutical formulation and administration may be found in "Remington: The Science and Practice of Pharmacy," Twentieth Edition, Lippincott Williams & Wilkins, Philadelphia, Pa. (1995). For instance, formulations such as the creams and lotions described above can be prepared by dispersing the sequestrant and enhancer, throughout the vehicle using conventional techniques, typically by levigating the sequestrant and enhancer with a small quantity of the cream or lotion base to form a concentrate, which is then diluted with additional cream or lotion base. Alternatively, a mechanical mixer may be used. Creams, lotions and other emulsions may also be prepared using a two-phase heat system, wherein oil-phase ingredients are combined under heat to provide a liquefied, uniform system. The aqueous-phase ingredients are separately combined using heat. The oil and aqueous phases are then added together with constant agitation and allowed to cool. At this point, concentrated agents may be added as a slurry. Volatile or aromatic materials can be added after the emulsion has sufficiently cooled, if desired.

The sequestrant and enhancer can also be incorporated into a gel formulation using known techniques. Two-phase gel systems generally comprise a suspension or network of small, discrete particles interpenetrated by a liquid to provide a dispersed phase and a liquid phase. Single-phase gel systems are formed by distributing organic macromolecules uniformly throughout a liquid such that there are no apparent boundaries between the dispersed and liquid phases. Suitable gelling agents for use herein include synthetic macromolecules (e.g., carbomers, polyvinyl alcohols and polyoxyethylene-polyoxypropylene copolymers), gums such as tragacanth, as well as sodium alginate, gelatin, methylcellulose, sodium carboxymethylcellulose, methylhydroxyethyl cellulose and hydroxyethyl cellulose. In order to prepare a uniform gel, dispersing agents such as alcohol or glycerin can be added, or the gelling agent can be dispersed by trituration, mechanical mixing or stirring, or combinations thereof.

Liposomes are microscopic vesicles having a lipid wall comprising a lipid bilayer, and can be used as drug delivery systems herein as well. Generally, liposome formulations are preferred for poorly soluble or insoluble pharmaceutical agents. Liposomal preparations for use in the instant invention include cationic (positively charged), anionic (negatively charged) and neutral preparations.

The formulations may also contain irritation-mitigating additives to minimize or eliminate the possibility of skin irritation or skin damage resulting from any of the components of the formulation. Suitable irritation-mitigating additives include, for example: α-tocopherol; monoamine oxidase inhibitors, particularly phenyl alcohols such as 2-phenyl-1-ethanol; glycerin; salicylic acids and salicylates; ascorbic acids and ascorbates; ionophores such as monensin; amphiphilic amines; ammonium chloride; N-acetylcysteine; cis-urocanic acid; capsaicin; and chloroquine. The irritant-mitigating additive, if present, may be incorporated into the present formulations at a concentration effective to mitigate irritation or skin damage, typically representing not more than about 20 wt. %, more typically not more than about 5 wt. %, of the formulation.

It is to be understood that while the invention has been described in conjunction with the preferred specific embodiments thereof, the foregoing description and the examples that follow are intended to illustrate and not limit the scope of the invention. Other aspects, advantages, and modifications within the scope of the invention will be apparent to those skilled in the art to which the invention pertains.

All patents, patent applications, and publications mentioned in this application are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

EXAMPLES

The following examples are put forth so as to provide those skilled in the art with a complete invention and description of how to make and use embodiments in accordance with the invention, and are not intended to limit the scope of what the inventors regard as their discovery. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

A composition according to the invention was prepared containing the following components:

| Water (DI) | 100 g | 92.0 wt. % |
| MSM (source, 99.9%) | 5.4 g | 5.0 wt. % |
| Disodium EDTA (source, 99.9%) | 2.6 g | 2.4 wt. % |
| Sodium alginate (source, 99%) | 0.7 g | 0.6 wt. % |

Preparation Procedure:
Dissolved 2.6 g NaEDTA in 100 g of DI Water (room temperature to 80 deg C.);
Dissolved 5.4 g MSM into the resulting solution; and
Dissolve the 0.7 g Na Alginate into the resulting solution.
The thickened solution so prepared was set aside for future use.

Example 2

An additional composition was prepared using the components and procedures of Example 1, with a greater fraction of sodium alginate as thickener. The amounts of the components in the final composition was as follows:

| Water (DI) | 100 g | 91.7 wt. % |
| MSM (source, 99.9%) | 5.4 g | 4.9 wt. % |
| Disodium EDTA (source, 99.9%) | 2.6 g | 2.3 wt. % |
| Sodium alginate (source, 99%) | 1.0 g | 1.1 wt. % |

Preparation Procedure:
Dissolved 2.6 g NaEDTA in 100 g of DI Water (room temperature to 80 deg C.);
Dissolved 5.4 g MSM into the resulting solution; and
Dissolved the 0.7 g Na Alginate into the resulting solution.
The thickened solution so prepared was set aside for future use.

Example 3

An additional composition was prepared using the components and procedures of Example 1, with a lesser fraction of sodium alginate as thickener. The amounts of the components in the final composition was as follows:

| Water (DI) | 100 g | 92.3 wt. % |
| MSM (source, 99.9%) | 5.4 g | 5.0 wt. % |
| Disodium EDTA (source, 99.9%) | 2.6 g | 2.4 wt. % |
| Sodium alginate (source, 99%) | 0.4 g | 0.3 wt. % |

Preparation Procedure:
Dissolved 2.6 g NaEDTA in 100 g of DI Water (room temperature to 80 deg C.);
Dissolved 5.4 g MSM into the resulting solution; and
Dissolved the 0.7 g Na Alginate into the resulting solution.
The thickened solution so prepared was set aside for future use.

Example 4

A composition according to the invention was prepared containing the following components:

| Water (DI) | 100 g | 92.3 wt. % |
| MSM (source, 99.9%) | 5.4 g | 5.0 wt. % |
| Disodium EDTA (source, 99.9%) | 2.6 g | 2.4 wt. % |
| Xanthan Gum (source, 99%) | 0.3 g | 0.3 wt. % |

Preparation Procedure:

Dissolve 2.6 g NaEDTA in 100 g of DI Water (room temperature to 80 deg C.);

Dissolve 5.4 g MSM into the resulting solution; and

Dissolved the 0.3 g Xanthan Gum into the resulting solution.

The thickened solution so prepared was set aside for future use.

Additional formulations were prepared with the following profile: Disodium EDTA, 2.5 wt. %; MSM, 2 wt. % to 8 wt. %; preservative (on FDA GRAS list); carrier—topical lotion vehicle; characteristics—emollient, moisturizing, harmless to stratum corneum; consistency—sufficient for ease of application; microbiological characteristics—preserved sufficiently to prevent contamination during manufacturing, shelf life, and topical administration to patients, passes USP test for antimicrobial efficacy and USP microbial limit test; shelf life—physically, chemically and microbiologically stable for at least six months at room temperature. Examples 5, 6, and 7 set forth the composition of three formulations prepared using the aforementioned parameters:

Example 5

Composition

| Ingredients | % W/W |
|---|---|
| Water Phase | |
| Methylsulfonylmethane | 5.0 |
| Disodium EDTA | 2.5 |
| Methyl Paraben | 0.2 |
| Carbomer 940 | 0.65 |
| Sodium hydroxide QS | Adjust pH to 6.5 |
| Purified Water QS | |
| Oil Phase | |
| Glyceryl Stearate-PEG 100 Stearate (Arlacel-165 by Uniquema America) | 2.2 |
| Isopropyl Palmitate (Crodamol IPP) | 1.5 |
| Ultra light Mineral oil (Carnation oil) | 3.0 |
| Stearic Acid | 0.75 |
| Emulsifying Wax (Cetearyl Alcohol (and) Polysorbate 60 (and) PEG-150 Stearate (and) Steareth-20) Polawax (Croda) | 1.0 |
| Petrolatum white | 0.5 |
| Propyl Paraben | 0.1 |
| Purified Water USP QS | Adjust batch |

A lotion was prepared using the above components and a standard compounding procedure for the preparation of topically administered lotions, as described in Martindale, supra.

Example 6

| Ingredients | % W/W |
|---|---|
| Water Phase | |
| Disodium EDTA | 2.5 |
| Methylsulfonylmethane | 5.0 |
| Methyl Paraben | 0.2 |
| Xanthan Gum (Keltrol-F) | 0.3 or 0.4 |
| Propylene glycol | 3.0 |
| Sodium hydroxide QS | Adjust pH |
| Purified Water QS | |
| Oil Phase | |
| Arlacel-165 (Glyceryl Monostearate) | 3.0 |
| White petrolatum | 3.0 |
| Isopropyl Palmitate (EMEREST 2316) | 2.0 |
| Propyl Paraben | 0.1 |
| Purified Water QS | Adjust batch |

A lotion was prepared using the above components and a standard compounding procedure for the preparation of topically administered lotions, as described in Martindale, supra.

Example 7

| Ingredients | % W/W |
|---|---|
| Water Phase | |
| Disodium EDTA | 2.5 |
| Methylsulfonylmethane | 5.0 |
| Methyl Paraben | 0.2 |
| PEG-4 (Polyethylene glycol 200) | 4.5 |
| Glycerin | 2.0 |
| Sodium hydroxide, QS | Adjust pH |
| Purified Water, QS | |
| Oil Phase | |
| Glyceryl Stearate SE (Cerasynt SD by Van Dyk or ISP) | 2.5 |
| Glycol Stearate (Protachem EGMS Protameen Chemicals) | 0.5 |
| PEG-75 (Lipoxol 3350 MED Sasol Germany) | 0.25 |
| PEG-6-32 (Carbowax PEG 540 blend) | 1.5 |
| Isopropyl Palmitate | 3.0 |
| Propyl Paraben | 0.1 |
| Purified Water USP QS | Adjust batch |

A lotion was prepared using the above components and a standard compounding procedure for the preparation of topically administered lotions, as described in Martindale, supra.

We claim:

1. A method for treating localized edema in a patient, comprising:
    topically applying to the patient at the site of the localized edema a composition consisting of
    (a) a therapeutically effective amount of a metal ion sequestrant, wherein the metal ion sequestrant is ethylenediamine tetraacetic acid (EDTA), and pharmacologically acceptable salts thereof,
    (b) an effective permeation-enhancing amount of a permeation enhancer selected from methylsulfonylmethane and a combination of methylsulfonylmethane and dimethylsulfoxide and
    (c) a pharmaceutically acceptable topical carrier consisting of one or more inactive additives,
    wherein the localized edema is caused by chronic venous insufficiency.

2. The method of claim 1, wherein the permeation enhancer is methylsulfonylmethane.

3. The method of claim 1, wherein the formulation is selected from a lotion, a cream, and a gel.

4. The method of claim 3, wherein the formulation is a lotion or a cream.

* * * * *